United States Patent [19]

Carilli

[11] Patent Number: 5,704,921
[45] Date of Patent: Jan. 6, 1998

[54] PREFILLED HYPODERMIC SYRINGE SYSTEM

[76] Inventor: Brian D. Carilli, 2150 Columbia St., Palo Alto, Calif. 94306

[21] Appl. No.: 539,965

[22] Filed: Oct. 6, 1995

Related U.S. Application Data

[63] Continuation-in-part of Ser. No. 443,120, May 17, 1995.

[51] Int. Cl.$^6$ .................................................. A61M 5/32
[52] U.S. Cl. ........................ 604/198; 604/110; 604/199; 604/187; 604/228
[58] Field of Search ............................. 128/763–766; 604/110, 191, 192, 195, 198, 199, 194, 187, 188, 218, 232–234, 236, 238, 239, 240, 255, 263, 272, 164, 165, 171, 228, 197, 205, 220, 221, 222, 224, 226

[56] References Cited

U.S. PATENT DOCUMENTS

| | | | |
|---|---|---|---|
| 3,115,133 | 12/1963 | Morando | 128/173 |
| 3,380,450 | 4/1968 | Adelberger | 128/218 |
| 3,498,295 | 3/1970 | Brickson et al. | 128/272 |
| 3,561,596 | 2/1971 | Knox et al. | 206/63.2 |
| 3,563,373 | 2/1971 | Paulson | 206/63.2 |
| 3,878,967 | 4/1975 | Joslin et al. | 221/88 |
| 3,939,833 | 2/1976 | Hansson et al. | 128/218 |
| 3,989,044 | 11/1976 | Meierhoefer | 128/218 |
| 4,014,330 | 3/1977 | Genese | 128/218 |
| 4,078,565 | 3/1978 | Genese | 128/220 |
| 4,130,117 | 12/1978 | Van Eck | 128/216 |
| 4,171,698 | 10/1979 | Genese | 128/218 |
| 4,180,070 | 12/1979 | Genese | 128/218 |
| 4,215,701 | 8/1980 | Raitto | 128/763 |
| 4,226,236 | 10/1980 | Genese | 128/218 |
| 4,236,516 | 12/1980 | Nilson | 128/216 |
| 4,334,536 | 6/1982 | Pfleger | 128/218 |
| 4,390,016 | 6/1983 | Riess | 604/236 |
| 4,573,977 | 3/1986 | Crawford | 604/212 |
| 4,723,937 | 2/1988 | Sarnoff | 604/90 |
| 4,723,945 | 2/1988 | Theiling | 604/232 |
| 4,908,022 | 3/1990 | Haber | 604/195 |
| 4,909,794 | 3/1990 | Haber et al. | 604/195 |
| 4,931,040 | 6/1990 | Haber et al. | 604/110 |
| 4,935,014 | 6/1990 | Haber | 604/195 |
| 4,968,303 | 11/1990 | Clarke et al. | 604/187 |
| 5,098,400 | 3/1992 | Crouse et al. | 604/192 |
| 5,135,514 | 8/1992 | Kimber | 604/240 |
| 5,147,325 | 9/1992 | Mitchell | 604/192 |
| 5,222,948 | 6/1993 | Austin | 604/213 |
| 5,269,766 | 12/1993 | Haber et al. | 604/198 |
| 5,273,542 | 12/1993 | Blake, III | 604/110 |
| 5,490,842 | 2/1996 | Volk et al. | 604/110 |

*Primary Examiner*—Corrine M. McDermott
*Assistant Examiner*—Cris L. Rodriguez
*Attorney, Agent, or Firm*—Flehr, Hohbach, Test, Albritton & Herbert

[57] ABSTRACT

A hypodermic syringe and method of filling the syringe with an injection fluid. The syringe includes a fluid chamber for retaining an injection fluid and a plunger assembly for expelling fluid from the chamber. The plunger assembly includes a plunger slidably disposed in the fluid chamber for creating positive pressures to cause ejection of a fluid from the chamber and an actuator coupled to the plunger for movement of the actuator between a first position with the actuator released for movement of the actuator through the fluid chamber relative to the plunger and a second position with the actuator in cooperative engagement with the plunger for driving the plunger to create the positive pressures.

17 Claims, 13 Drawing Sheets

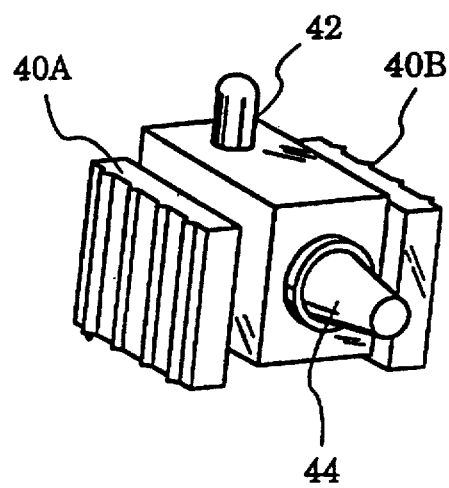
FIG. 3
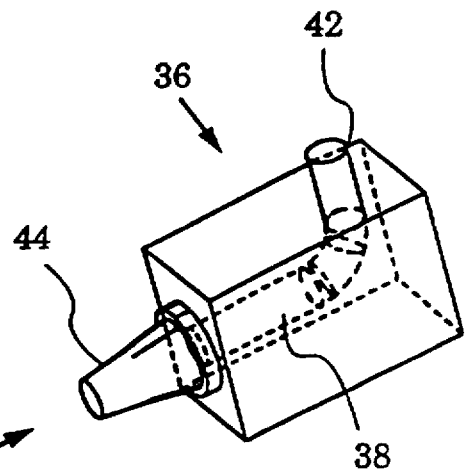
FIG. 4
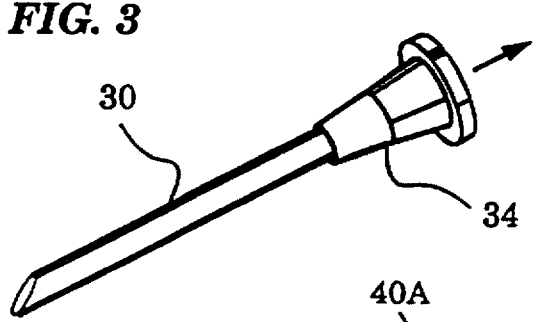
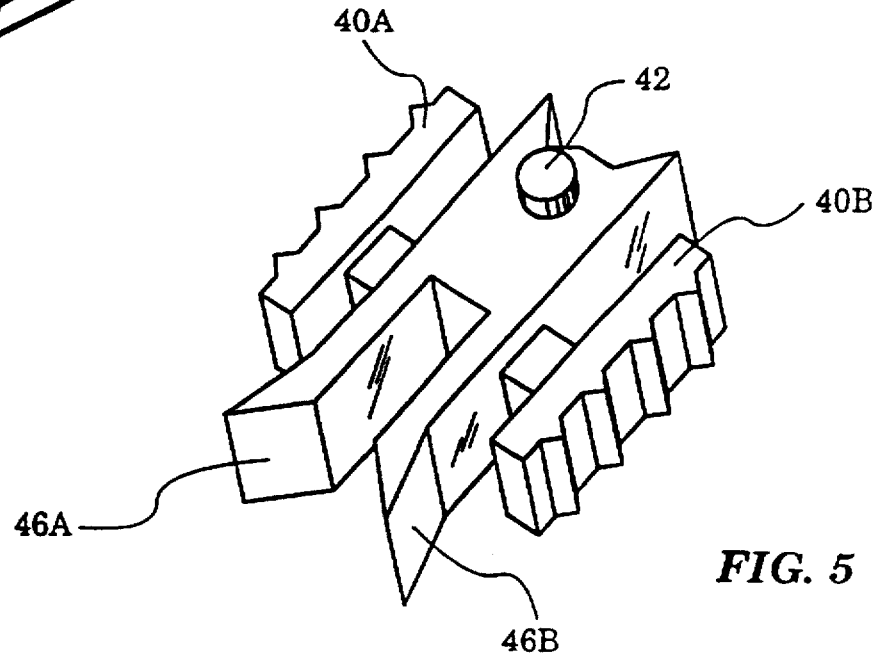
FIG. 5

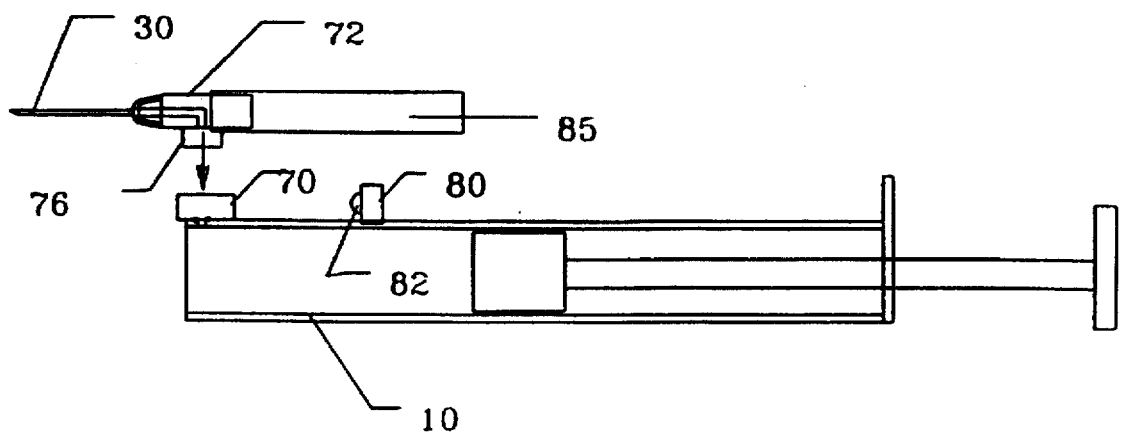
FIG._12
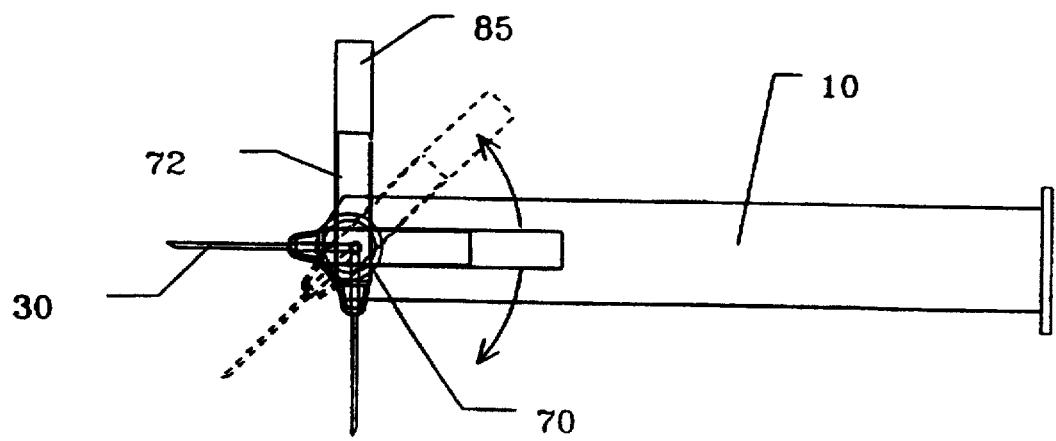
FIG._13

PREFILLED HYPODERMIC SYRINGE SYSTEM

CROSS REFERENCE TO RELATED APPLICATIONS

This application is a continuation-in-part of U.S. Ser. No. 08/443,120 filed May 17, 1995, the disclosure of which is incorporated herein by reference.

BACKGROUND OF THE INVENTION

The present invention relates in general to the field of hypodermic needles, and in particular, to a hypodermic needle assembly having a prefilled syringe.

Hypodermic syringes having prefilled barrels and prefilled cartridges for use with syringe systems provide an alternative to filling the hypodermic needle on site. Prefilled syringes minimize packaging by eliminating the need for a separate vial of medication. This is of particular importance in the emergency room or ambulance where a variety of equipment must be stored in a limited area. In addition, the step of transferring the medicine from the vial to the syringe is eliminated. Reducing the number of steps required for an injection is of particular importance in the emergency room, hospital, ambulance or other environment where the medicine must be injected as quickly as possible. The large-bore needles used to extract the fluid from the vial are also eliminated, reducing the risks of accidental needle pricks during the handling of the syringe. The risk of contamination of the medicine is also reduced.

With many prefilled syringes, the barrel includes a membrane which seals the liquid within the barrel. The membrane may be ruptured, releasing the fluid for injection, by using a needle assembly to pierce the membrane or by applying sufficient pressure to burst the membrane. Typically, the prefilled syringe is supplied with the plunger projecting from the rear of the barrel, requiring additional space for packaging, shipment and storage of the device. Additional packaging may be required to secure the plunger in the extended position and prevent premature emptying of the barrel. Moreover, care must be taken to prevent damaging the plunger prior to use. Some available syringes include an outer shell which is coupled to a piston head. The fluid is dispensed by sliding the outer shell relative to the barrel to depress the piston head. Although this type of prefilled syringe may be less susceptible to damage, the outer shell must be retained in an extended position until the syringe is used.

Prefilled cartridges provide protection against contamination of the medicine and minimize the space required for storage and shipment of the cartridges since the cannula and plunger elements are separate from the cartridge. However, the overall space occupied by the different components of the syringe assembly is not reduced. Further, the prefilled cartridge must be loaded into a syringe assembly prior to use, requiring an additional step. The risk of contamination may also be increased unless care is taken to protect the critical surfaces of the syringe assembly and/or cartridge from airborne contaminants.

The hypodermic needle is one of the most dangerous tools in modern medicine. Common microorganisms, including deadly viruses, are known to be communicable through infected hypodermic needles. In the urgent environment of ambulances or hospital emergency rooms, used and exposed hypodermic needles present a hazard to medical workers or patients. An accidental stab or scratch produced by such needles can introduce dangerous viruses or other contaminants directly into a person's blood stream. Therefore, there is a need for protecting medical personnel and patients from exposed hypodermic needles.

Many solutions have been proposed to solve the problem. Most involve very complex, spring-loaded mechanisms for automatic needle retraction after injection. These are unsuitable for disposable syringes because of cost considerations. In addition, their intricate construction increases the chances of malfunctioning.

Another group of solutions proposes a manual retraction systems. These tend to be very inconvenient and cumbersome to operate. The number of steps to be performed by the person administering an injection is drastically increased. In addition, manual retraction systems, as well as the automatic ones referred to above, increase the number of parts on the front of the syringe barrel. This limits the range of angles from which the needle can be introduced under the patient's skin. In fact, with all the fixtures and attachments required for safe needle retraction, the operator is restricted to a ninety degree angle of entry. Under this angle the needle penetrates deep under the patient's skin and is frequently hard to withdraw.

Of course, the advantage of a shallower angle of entry has been recognized in the art. Many old-fashioned syringes have a needle-mounting snout located off-center for this very reason. Nonetheless, for technical reasons having to do with the retraction mechanism, no state of the art solution incorporates the concept of shallow entry angle and protection of the hypodermic needle.

SUMMARY OF THE INVENTION

In summary, one embodiment of the present invention combines the innovation of mounting a hypodermic needle on one side of a syringe, rather than in the center, with the idea of encasing or removing the needle after it has been used. Therefore, one embodiment of this invention teaches that a needle mounted on a carriage can slide within a sheath, where this sheath is mounted on the side of a syringe or other chamber filled with fluid. The needle can slide to one of three positions; in the first position, it is closest to the front of the syringe, and it is ready to be used. In this position, the carriage mounted to the needle is in the right position to trigger the chamber to open a side outlet and allow fluid to pass through the outlet, through a duct in the carriage, and out through the needle. In the second position, the outlet is closed, and the needle and carriage are reversibly retracted into the sheath. In a third position, the outlet is also closed, and the needle and carriage are retracted, even deeper into the sheath, irreversibly, so that the needle can not be made to protrude. This is the disposal position. In the most preferred embodiment the carriage and needle are locked into these three positions along a sliding track by means of flexible legs on the carriage which protrude into notches on the track. The operator frees the carriage and needle from these notches by depressing buttons to compress the legs.

This invention teaches that the entire sheath containing the carriage and needle may be removed from the chamber of fluid. Alternatively, the carriage and needle unit may be removable from the sheath. Both of these variations use reversible mounting mechanisms, such as mechanical snapping-on of parts.

In another embodiment, the present invention provides a syringe system which is particularly useful for prefilled applications where the syringe is supplied with the chamber of the syringe filled with an injection fluid. The fluid chamber has an outer wall and an outlet for dispensing fluid from the chamber. The syringe also includes a plunger assembly for expelling fluid from the chamber. The plunger assembly includes a plunger which is slidable through the chamber for creating positive pressures to cause ejection of a fluid from the chamber. The assembly also includes an actuator coupled to the plunger for movement of the actuator between a first position, with the actuator released for movement through the chamber relative to the plunger, and a second position, with the actuator in cooperative engagement with the plunger for driving the plunger through the chamber to create the positive pressures.

The method of this embodiment of the invention includes the steps of forming a chamber for retaining an injection fluid and slidably positioning a plunger assembly in the chamber. The plunger assembly includes a plunger which is spaced from an outlet of the chamber and an actuator for driving the plunger through the chamber. At least a portion of the actuator is initially positioned within the chamber between the outlet and the plunger. The method also includes the steps of substantially sealing the outlet of the chamber and injecting a fluid into the chamber between the outlet and the plunger. Preferably, the outlet is sealed by positioning the actuator in sealing engagement with the outlet of the chamber. Prior to use, the actuator is moved into interengagement with the plunger so that the actuator may be used to move the plunger through the chamber.

BRIEF DESCRIPTION OF THE DRAWINGS

Additional objects and features of the invention will be more readily apparent from the following detailed description and appended claims when taken in conjunction with the drawings, wherein:

FIG. 3 is a perspective view of a part of the embodiment of FIG. 1, the carriage containing the needle;

FIG. 4 is a perspective view of how the needle in the embodiment of FIG. 1 is attached to the needle carriage;

FIG. 5 is a perspective view of the locking legs of the carriage of the embodiment of FIG. 1;

FIG. 12 is a top plan view of another embodiment of the invention;

FIG. 13 is a top plan view of another embodiment of the invention, shown with the needle oriented in a plurality of positions relative to the fluid chamber;

DESCRIPTION OF THE PREFERRED EMBODIMENTS

Figure 1:
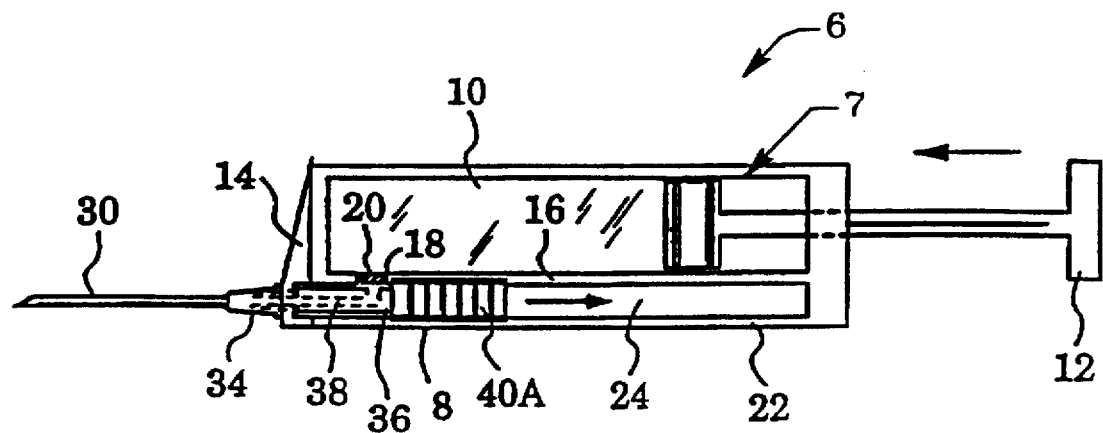
FIG. 1 is a side view of the preferred embodiment of the invention.

Reference will now be made in detail to the preferred embodiment of the invention, which is illustrated in the accompanying figures. Turning now to the drawings, wherein like components are designated by like reference numerals throughout the various figures, attention is directed to FIGS. 1–6.

FIGS. 1–6 show an embodiment of a hypodermic syringe 6 in accordance with the invention. The hypodermic syringe 6 may be used to extract fluids or to inject fluids supplied in a vial, ampule or the like which is separate from the syringe. The syringe also may be prefilled, although the modifications shown in FIGS. 14–24 are preferred for prefilled applications. The hypodermic syringe 6 generally includes a syringe body 7 and a needle assembly 8 having a needle 30 which may be easily moved from the extended position shown in FIG. 1 to a retracted position with the contaminated needle safely contained within a protective sheath 22. As is shown in FIG. 1, the syringe body 7 and needle assembly 8 are formed as a single unit. After the used needle 30 has been retracted within the sheath 22, the entire unit may be safely discarded. In alternative forms of the invention, such as those shown in FIGS. 8–11, the syringe body 7 and needle assembly 8 may be separate components with the needle assembly being detachable from the syringe body for disposal of the needle. Providing the needle assembly 8 as a separate component is particularly useful when the hypodermic needle is used to extract a sample of fluid, such as blood, from the patient's body.

Turning particularly to FIG. 1, syringe body 7 includes a chamber 10 and a plunger 12 extending through the chamber 10. The chamber 10 is filled with injection fluid, although in applications where the hypodermic is used to collect fluids the chamber 10 may be empty. Near the front end 14 of chamber 10, within a side wall 16, there is an outlet 18. A valve, such as a check valve 20, is fixed in outlet 18 to control the flow of fluid through outlet 18. The chamber 10 has a central axis substantially aligned with the plunger 12.

The sheath 22 of the needle assembly 8 is positioned to one side of the chamber 10, with the central axis of the sheath offset from the central axis of the chamber 10. With this configuration, the syringe body 7 will not interfere with the orientation of the needle relative to the patient's body, allowing the needle to be inserted into the skin at a substantially small angle. In addition, this configuration is particularly suitable for embodiments of the invention in which the sheath is detachable from the chamber 10. Although positioning the needle assembly 8 to one side of the syringe body 7 is preferred, it should be understood that in other modifications of the invention the syringe body 7 may extend circumferentially around a major portion of the needle assembly 8 if desired. In the present embodiment, the sheath 22 is defined by the side wall 16 of the chamber 10 and two spaced flanges depending from the side wall 16 to form a U-shaped channel or recess 24. Alternatively, the sheath may include a bottom wall spaced from the side wall 16 of the chamber. Depending upon the length of the chamber 10 and the size of the needle 30, the recess 24 may extend along the entire length of the chamber as shown in FIG. 1 or the recess 24 may be shorter or longer than the chamber. In the embodiment shown in FIGS. 1–6, the sheath 22 is permanently mounted to or integrally or monolithically formed with the chamber 10. In other embodiments of the invention, the sheath 22 may be removably mounted to the chamber 10.

A carriage 36 mounted within recess 24 may be moved from one end of recess 24 to the other. The needle 30 is attached at the front end of carriage 36. The carriage preferably includes a conduit for delivering fluid to the needle 30. In the embodiment shown in FIG. 1, carriage 36 has a duct 38 which extends from the valve 20 to the needle 30, presenting the only path for fluid to flow between chamber 10 and needle 30. Two buttons 40A and 40B are provided on either side of the carriage 36 for controlling the position of carriage 36. They extend outside recess 24, with the stems of the buttons engaging two lateral slots 26 formed in the walls of sheath 22. Lateral slots 26 extend along the length of recess 24 and end before reaching the front end of recess 24. The carriage 36 may be moved along the recess 24 by sliding the buttons 40A and 40B along the slots 26. The front ends of the slots 26 prevent the carriage from failing out of recess 24.

Figure 2:
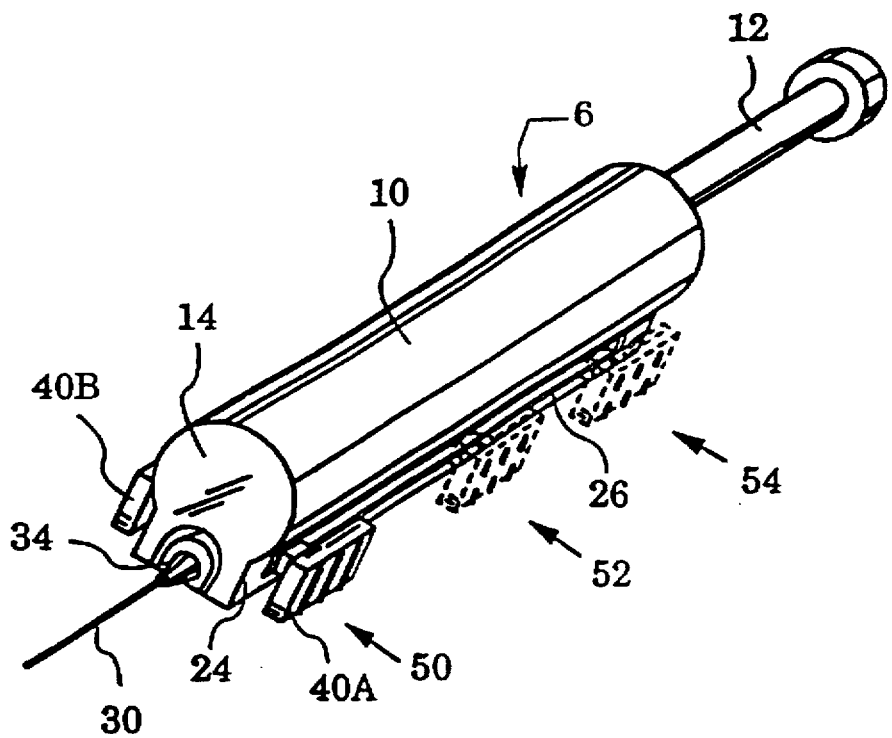
FIG. 2 is a perspective view of the embodiment of FIG. 1, showing three states for the needle.

As is shown in FIG. 2, the carriage 36 may be moved within recess 24 between three positions. In a ready-position 50, carriage is near the front end 14 of chamber 10. Duct 38 is aligned with the chamber outlet 18 (FIG. 1) and positioned to open valve 20 (FIG. 1), allowing fluid to flow from the chamber 10 to needle 30. In the standby-position 52, carriage 36 and needle 30 are completely retracted into recess 24, protecting the needle 30 against contamination. With the carriage 36 in the stand-by position, the needle 30 is positioned within the sheath 22 for the safe storage and handling of the unused device. However, in other forms of the invention the needle 30 may be supplied in the extended position shown in FIG. 1 with a removable sleeve covering and protecting the needle prior to use as is known in the art. As is described in more detail below, the carriage may be easily moved from the stand-by position 52 to the ready-position 50. After the needle 30 has been used, the carriage 36 may be retracted to the disposal-position 54. Unlike the stand-by position 52, the carriage 36 may not be moved forwardly from the disposal position 54 to either the stand-by position 52 or the ready position 50.

FIGS. 3 and 4 show a more detailed view of carriage 36. Buttons 40A and 40B jut out from either side of the carriage. On the upper surface of carriage 36 facing chamber 10, duct 38 ends in a dome-shaped distal end 42 formed to open the valve 20 and permit discharge of the fluid from the chamber 10. A nose-shaped connector 44 coupled to the proximal end of the duct 38 projects from the front end of the carriage 36. Needle 30 has a receptor 34 on its end which attaches firmly to connector 44. In this embodiment, connector 44 is a regular tube for snapping on hypodermic needles by their receptor 34. This snap-on mechanism is well-known in the art.

FIG. 5 shows the locking feature of carriage 36 which secures the carriage 36 in each of the positions 50, 52 and 54 shown in FIG. 2. Two elastic legs 46A and 46B extend outwardly from the back end of the carriage 36. Legs 46A and 46B are tapered, and jut out slightly beyond the width of carriage 36. Buttons 40A and 40B are attached to legs 46A and 46B in such a way that when button 40A is depressed, leg 46A bends inward, so that it no longer juts outward, and button 40B depresses leg 46B in a similar way. Of course, there are many other mechanical solutions for a locking mechanism adaptable to carriage 36. Corresponding grooves, notches, catches and other provisions for actuating such locking mechanisms can be easily incorporated on the side of the syringe or inside sheath 22.

Figure 6:
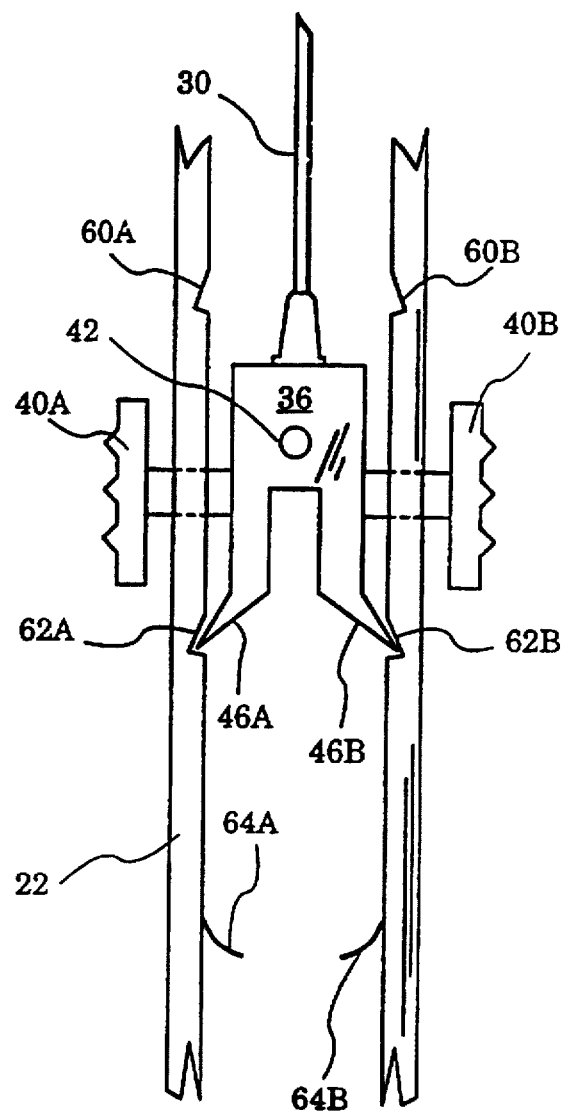
FIG. 6 is a cross-section view of the entire locking mechanism of the embodiment of FIG. 1.

The operation of the locking mechanism is shown in FIG. 6. The walls of the recess 24 are formed with a plurality of notches shaped to engage the legs 46A and 46B of the carriage 36 and retain the carriage in one of the positions 50 and 52. The first two notches, which are the ready-position notches 60A and 60B, are closer to front end 14. When the legs 46A and 46B engage the notches 60A and 60B, the carriage 36 is held securely in the ready position 50. The engagement between the legs and the notches prevents the carriage 36 from moving backwards, withstanding the force required to insert the needle into the patient's body. Once needle 30 has been used, buttons 40A and 40B are pressed together to disengage the legs 46A and 46B from the notches 60A and 60B and the carriage 36 may be moved backwards. The notches 62A and 62B engage the legs 46A and 46B to retain the carriage 36 in the standby-position, preventing forward and backward movement of the carriage until the buttons 40A and 40B are depressed. When the operator moves carriage 36 backwards to disposal-position 54, the legs 46A and 46B are moved past two tabs 64A and 64B which catch carriage 36 and prevent it from moving forwards again. In this embodiment, the tabs are leaf springs. However, the configuration of the tabs are subject to considerable variation. Because sheath 22 is closed at the back end, carriage 36 is thereby fixed in position; there is no mechanism for moving it either forwards or backwards. However, in other embodiments of the invention the sheath may be open at its back end to allow carriage 36 and needle 30 to be removed from the recess 24.

Figure 7:
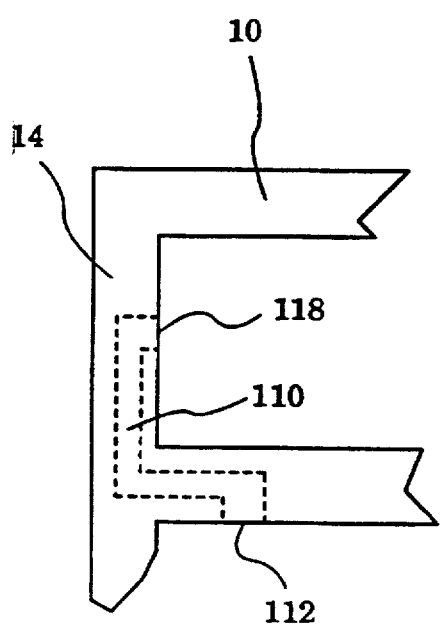
FIG. 7 is a side view of an alternative embodiment of the invention.

The outlet 18 and duct 38 provide a passageway for transporting fluid between the chamber 10 and the needle 30. In the embodiment shown in FIGS. 1–6, the chamber 10 is formed with an outlet which extends straight through the chamber wall. FIG. 7 shows an alternative embodiment of the chamber 10 in which the outlet 18 is replaced by a conduit 110 extending from an interior opening 118 in the front wall of chamber 10 to an exterior opening 112 on the side wall 16. With this embodiment, all the fluid held within chamber 10 may be injected into the patient's body. With the embodiment shown in FIGS. 1–6, the fluid between the front end 14 of the chamber and outlet 18 would become trapped within the chamber once the plunger 12 had passed outlet 18.

Figure 8:
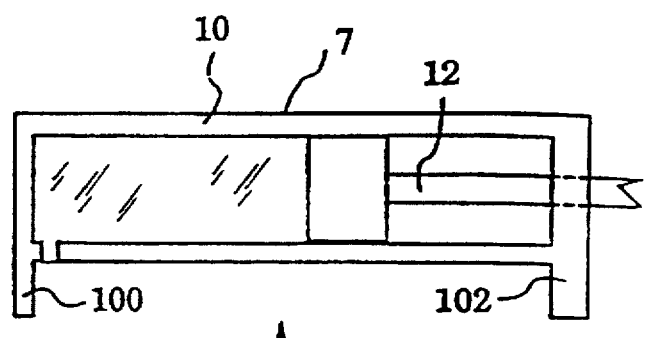
FIG. 8 is a side view of an alternative embodiment in which the sheath is removable from the syringe.

FIG. 8 shows an embodiment of the invention in which the needle assembly 8 is detachable from chamber 10. In this embodiment, needle assembly 8 includes a sheath 22 which is mounted onto chamber 10 by a secure mounting system which allows the operator to remove sheath 22 after needle 30 has been used and safely retracted within the sheath. As is shown in FIG. 8, chamber 10 has a front wall 100 and a back wall 102 which extend beyond the side wall of the chamber. The sheath 22 may be snapped into the space between the front and back walls 100 and 102. The sheath 22 may be easily detached from the chamber 10 by pulling the sheath from between the front and back walls. In other embodiments, other means may be used to removably or permanently couple the sheath to the chamber. For example, sheath 22 may be screwed on, twisted on, slid on, magnetically placed onto chamber 10, or permanently affixed by adhesive, ultrasonic welding, and the like instead of snapping the sheath 22 in place.

Figure 9:
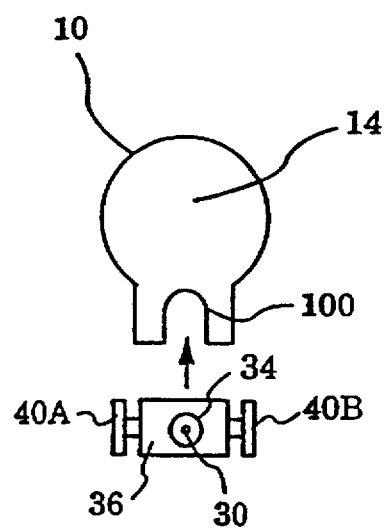
FIG. 9 is a frontal view of the embodiment of FIG. 8.

FIG. 9 shows a frontal view of the embodiment of FIG. 8. Front wall 100 has a mouth 104 which allows the needle 30 to project from the front wall 100. Preferably, the carriage 36 is prevented from passing through the mouth 104. However, if desired the front ends of slots 26 may be used to interrupt the forward progress of the carriage. In the present invention, the mouth 104 is generally U-shaped slot extending upwardly from the lower edge of the front wall 100. Alternatively, the mouth may be provided as an aperture formed in the front wall 100.

Figure 10:
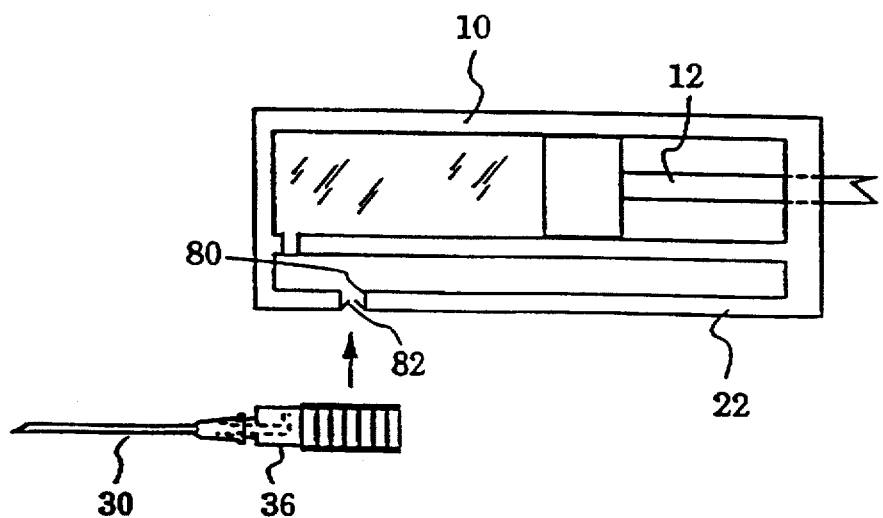
FIG. 10 is a side view of an alternative embodiment in which the carriage is removable from the sheath.

FIG. 10 shows another embodiment of the invention in which sheath 22 is integrally formed with or permanently mounted to the fluid chamber 10. The lower surface (not shown) of the sheath is open for insertion of the carriage 36 into the sheath 22. Sheath 22 has an opening 80 through which the stems of the buttons 40A and 40B may pass. Opening 80 has a pair of one-way keepers or tabs 82 which bend inward when the carriage 36 is inserted into the sheath. After the stems of the buttons 40A and 40B pass through the opening 80, the keepers 82 return to their original shape and block carriage 36 from coming out of sheath 22 again. In this modification, the sheath 22 may consist of two spaced flanges depending from the chamber 10, with the engagement between the buttons 40A and 40B and the slots retaining the carriage 36 in the sheath. Alternatively, the sheath may have a bottom wall which is formed with an opening of sufficient size to receive carriage 36.

Figure 11:
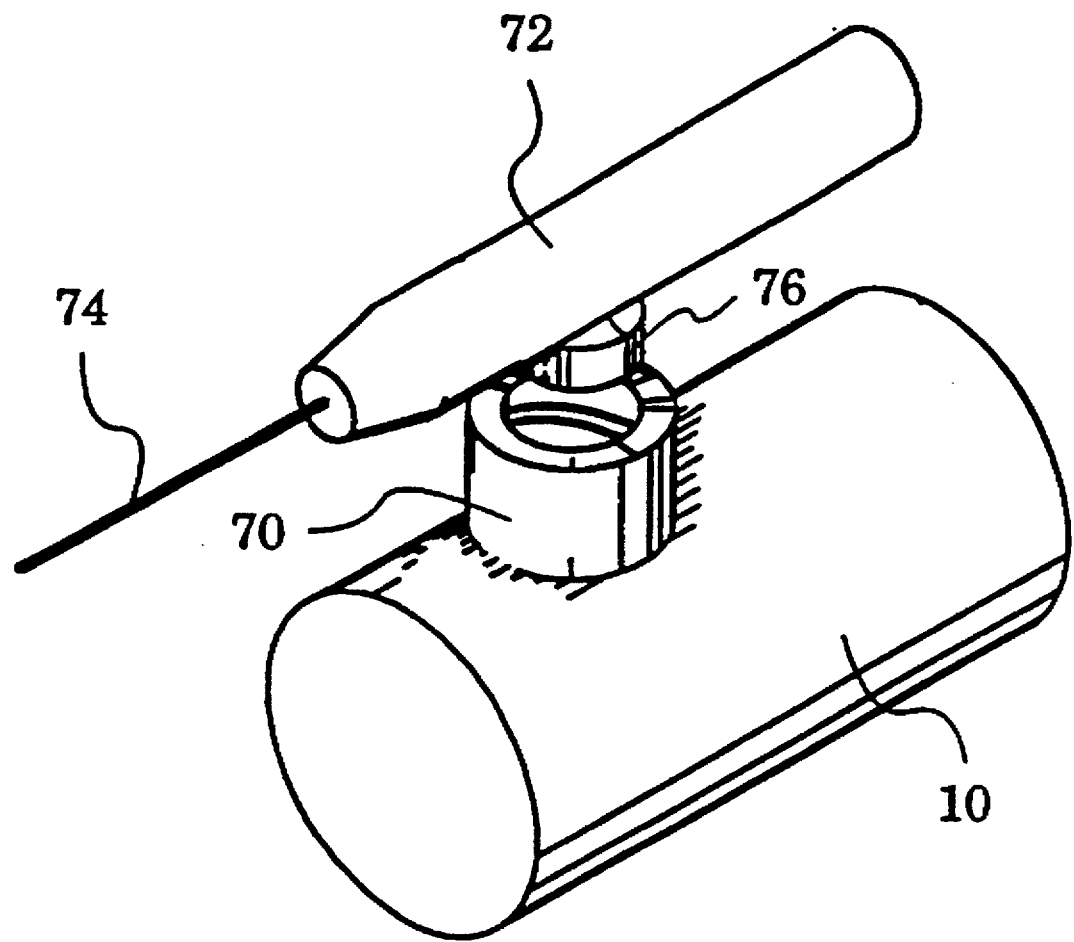
FIG. 11 is a perspective view of an alternative embodiment of the invention.

The advantages of positioning the needle 30 to the side of the fluid chamber 10 are further described in relation to the modifications shown in FIGS. 11–13. With these embodiments, the needle carriage may be efficiently mounted to the chamber 10 and removed from the chamber after the needle 30 has been used. A shallow angle of entry may be obtained by orienting the assembly with the needle carriage between the patient's skin and the chamber 10. As is described in relation to FIG. 13, the needle position is not restricted to a parallel orientation relative to the chamber 10.

In the modification shown in FIG. 11, carriage 72 does not slide along the syringe. Instead, the carriage 72 is mounted by screwing into the syringe. In this embodiment, chamber 10 has a socket 70 jutting out and surrounding an outlet (not shown). The spout 76 of carriage 72 securely engages the socket 70. In the present embodiment, the spout 76 and socket 70 are formed with screw threads which cooperate to securely retain the spout within the socket. However, various other means may be used to secure the carriage to the chamber 10 including, but not limited to, snap beads, slot-key structures, locking nuts, and the like. Carriage 72 is thereby mounted securely onto chamber 10, and duct 38 (not shown) is aligned with the outlet of the fluid chamber. After needle 74 has been used, carriage 72 is screwed off and disposed. This embodiment saves materials and costs of manufacturing.

In the embodiment shown in FIG. 12, carriage 72 is mounted to the fluid chamber 10 by positioning spout 76 in the mounting ring or socket 70 on the chamber 10. The spout 76 and socket 70 are formed with cooperating engagement means suitable for securing the two members together such as screw threads, snap beads, slot-key structures, locking nuts, and the like. The back surface of needle carriage 72 is shaped to engage a locking mount 80 carried by the fluid chamber 10 to prevent rotational movement of the needle carriage 72 relative to the chamber 10 during insertion of the needle 30. In the illustrated embodiment, the protruding bead 82 on the locking mount 80 seats in a pocket 79 formed in the back surface of the needle carriage 72. However, it should be understood that the position of the bead 82 and the pocket 79 may be reversed. Moreover, other suitable engagement means may be used to anchor the needle carriage 72 to the locking mount 80.

A U-shaped sheath 85 is slidably mounted to the needle carriage 72. After the needle has been used, the sheath 85 slides along the carriage 72 and across the needle 30 until the contaminated tip of the needle is positioned within the sheath. Unlike the needle assemblies of the prior art, mounting the needle carriage to the side of chamber 10 allows the sheath to be separate from the chamber 10, providing greater flexibility in the size of the sheath 85 and the overall assembly.

The needle position is not restricted to a parallel orientation relative to the chamber 10. FIG. 13 shows an embodiment of the invention in which the needle 30 may be held in several positions such as parallel to the longitudinal axis of the chamber 10, perpendicular to the chamber 10 or at any other angle. The needle carriage 72 is mounted to the fluid chamber 10 through the interengagement of a mounting ring or socket 70 and a spout 76. The mounting ring 70 is indexed to interlock with the spout 76 on the carriage and securely retain the needle in several different positions. Orienting the needle 30 at an angle relative to the axis of the chamber 10 allows pressure to be placed on the chamber 10 during use of the assembly, such as when extracting blood, without forcing the needle further into the patient. Various means may be used to secure the spout 76 and indexed mounting ring 70 together. For example, the mounting ring 70 may include a slot-key structure configured to permit rotation of the socket between two or more interlocked positions. In another example, the socket may be formed with a button which projects through a hole formed in the mounting ring 70 to lock the needle carriage in the desired position. By depressing the button, the button may be released and the spout rotated to bring the button into engagement with another hole formed in the mounting ring. In addition, other suitable means may be used for interlocking the spout and the mounting ring in one of several different positions.

Figure 13A:
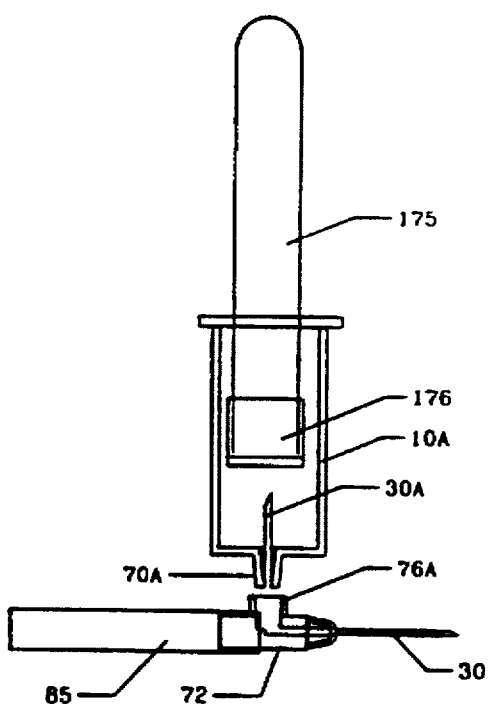
FIG. 13A is a side plan view of another embodiment of the invention.
Figure 26:
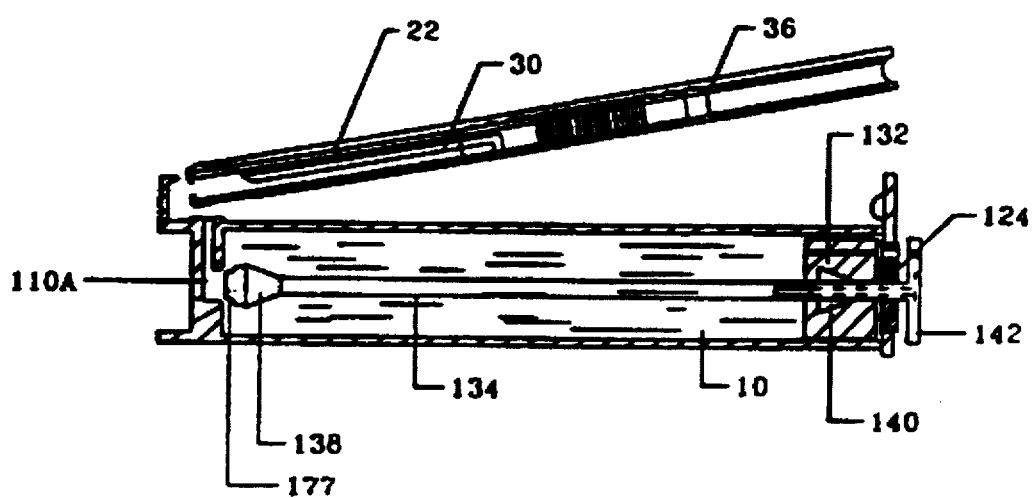
FIG. 26 is a cross-sectional view of another embodiment of the invention, shown with the needle assembly being applied to the chamber.

FIG. 13A shows an embodiment of the invention in which the needle 30 has a perpendicular orientation relative to the chamber 10A. This embodiment is particularly suitable for use with a sealed vacuum container 175 which is often used when extracting a sample of blood. The container 175, which is sealed with a rubber top 176, is moved into the chamber 10A until the needle 30A pierces the top 176. The needle carriage 72 is mounted to the chamber 10A using suitable securement means such as the spout 70A of the chamber and the socket 76A of the needle carriage 72A. Blood or other fluid drawn into the needle 30 is transported through the needle 30A and into the container 175. After the container 175 has been filled, the protective sheath 85 may be moved onto the needle 30 to provide protection against accidental contact with the needle.

In the embodiments shown in FIGS. 11-13, the mounting ring or socket 70 is provided on the fluid chamber 10 while the spout 76 is positioned on the needle carriage 72. However, it should be understood that in other modifications the needle carriage 72 may have the mounting ring 70 while the fluid chamber 10 may be formed with the spout.

The protection system of the syringe of the present invention should not be limited to the specific embodiments shown in the Figures. Many other variations are possible. For example, the check valve can be replaced with a slide gate, or with any other mechanism which synchronizes the opening of an outlet for fluid with the presence of an external duct to receive the fluid; another alternative is a film covering which is penetrated once the outlet contacts the external duct. In fact, because of the presence of the plunger, fluid will not flow unless the plunger is pushed or pulled, so the check valve may be even unnecessary. Mother variation is a different mechanism for locking the carriage. For example, the legs could jut into notches in the lateral slots, or notches in the side wall, rather than notches in the walls of the recess. The buttons 40A and 40B may be replaced by one button on the top which controls one leg. In fact, any locking mechanism can be used which locks a sliding carriage to a track based on the position of the carriage within the track, such as a retracting pen mechanism. Similarly, the tabs which prevent the carriage from sliding out once the carriage attains the "disposal-position" may be any mechanism which allows unidirectional sliding of an object within a track.

FIGS. 14-21 show another embodiment of a hypodermic syringe 6 in accordance with the invention. The syringe 6 is particularly suitable for prefilled applications where the syringe is supplied to the consumer with the chamber filled with an injection fluid. The prefilled chamber offers several advantages such as the elimination of a separate package for the injection fluid and the elimination of the step of filling the chamber prior to the injection. The chamber may be supplied with a precisely measured amount of the fluid, further improving the efficiency of the injection process by eliminating the step of carefully measuring the amount of fluid which is drawn into the chamber from the supply vile.

The prefilled hypodermic syringe 6 shown in FIGS. 14-21 generally includes a chamber 10 filled with a selected fluid and a needle assembly 8. As is described in more detail in relation to FIGS. 8-9, the needle assembly 8 generally includes a protective sheath 22 which is detachable from the chamber 10 for disposal. However, if desired the sheath 22 and chamber may be a unitary structure as shown in FIGS. 1-6 or other configurations of the needle assembly 8, such as those shown in FIGS. 10-13, may be employed. The needle 30 is safely retained in the protective sheath 22 until the needle carriage 36 is secured in the position shown in FIG. 19. After the injection, the needle carriage 36 may be released and moved to the disposal position shown in FIGS. 20 and 21, with the needle safely retracted into the protective sheath.

Figure 19:
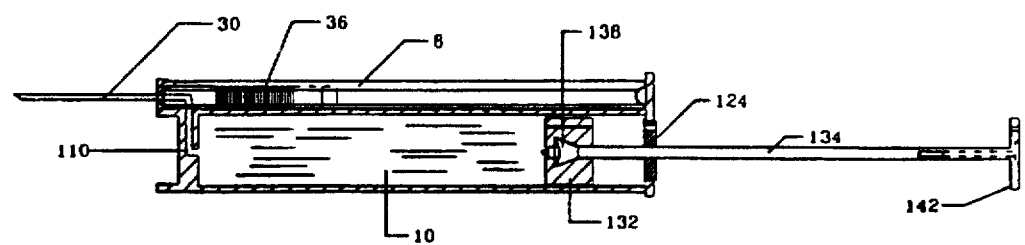
FIG. 19 is a cross-sectional view of the syringe assembly of FIG. 14, shown prepared for an injection.

In this embodiment, chamber 10 is formed with the conduit 110 (shown particularly in FIG. 7) for transporting fluid from an opening 118 in the front wall of the chamber to the duct 38 (FIG. 4) formed in the needle carriage 36 when the carriage is retained in the position shown in FIG. 19. The rear wall of chamber 10 is formed with an opening 122 which is sealed by a cap 124.

Figure 14:
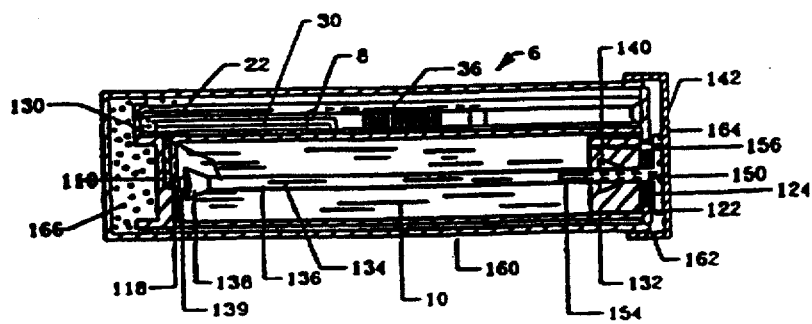
FIG. 14 is a cross-sectional view of a syringe assembly in accordance with another embodiment of the invention, shown packaged for shipment and storage.
Figure 15A:
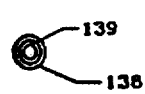
FIGS. 15A and 15B are end views of the plunger assembly of FIG. 14.
Figure 15B:
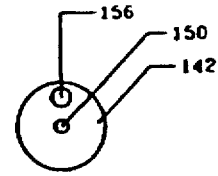
Figure 17:
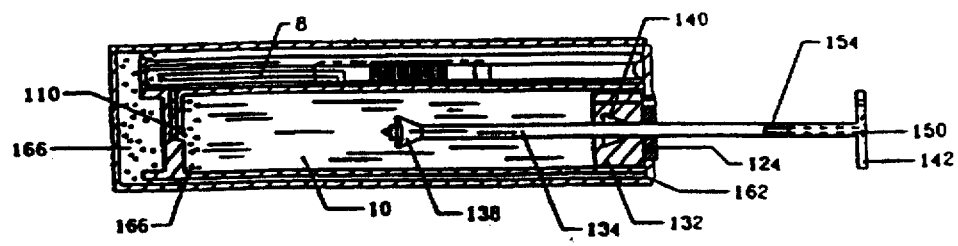
FIG. 17 is a cross-sectional view of the syringe assembly of FIG. 14, shown with the actuator of the plunger assembly partially retracted.
Figure 18:
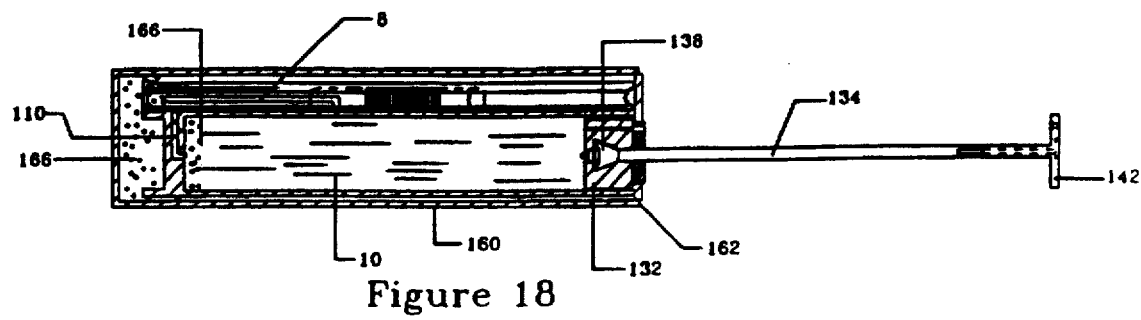
FIG. 18 is a cross-sectional view of the syringe assembly of FIG. 14, shown with the actuator of the plunger assembly fully retracted.

Syringe 6 includes a plunger assembly 130 having a plunger head 132 and an actuator 134. The actuator is initially separate from and movable relative to the plunger 132. FIG. 14 shows the actuator 134 substantially disposed in the chamber 10, while FIGS. 17 and 18 show the actuator in partially and fully retracted positions, respectively, relative to the chamber. Actuator 134 includes an elongated body 136 which extends through openings in the plunger head 132 and cap 124. The elongate body has a shaped tip 138 (FIG. 15A) which is adapted to seal the opening 118 formed in the front wall of the chamber 10 when the actuator is fully inserted in the chamber as shown in FIG. 14. In this embodiment, the shaped tip 138 includes a plug 139 which extends through the opening 118, engaging the inner wall of the conduit 110 to provide an effective seal. The plug 139 is removed from the opening 118 when the actuator 134 is retracted, breaking the seal. The tip 138 and the conduit opening 118 may have other shapes within the scope of the invention. Moreover, other means may be used to seal conduit 110 although sealing the conduit 110 with the shaped tip 138 is preferred. FIG. 27 shows another embodiment of a shaped tip 138 which includes a plug 177 shaped to seal with the enlarged opening of a laterally extending conduit 110A.

The tip 138 is shaped to engage the plunger 132 when the actuator is moved to the fully retracted position shown in FIG. 18. It is to be understood that the configuration of tip 138 and plunger head 132 is subject to considerable variation within the scope of this invention. In the embodiment shown in particularly in FIG. 14, the tip 138 has a barbed configuration which allows the tip 138 to be pulled into a cooperatively-shaped socket 140 formed in the plunger 132. The tip 138 and socket 140 are shaped to interengage and prevent removal of the tip from the socket when the actuator 134 is moved in the opposite direction relative to the chamber 10. Once the tip 138 is securely retained in the socket 140, the actuator 134 may be used to drive the plunger head 132 through the chamber 10 to inject the fluid through needle 30. The cap 124 provides stability when the actuator 134 is retracted into engagement with the plunger 132 or used to drive the plunger head through the chamber 10. In other embodiments of the invention, other means may be used to reinforce the actuator 134. Actuator 134 preferably includes means such as push plate 142 to facilitate the manipulation of the plunger assembly 130 when retracting the actuator 134 from the chamber 10 into engagement with the plunger 132 or driving the plunger 132 through the chamber. In the present embodiment, the push plate 142 is in the form of a planar disc. However, the push plate 142 may have other shapes as is known in the art.

Figure 16A:
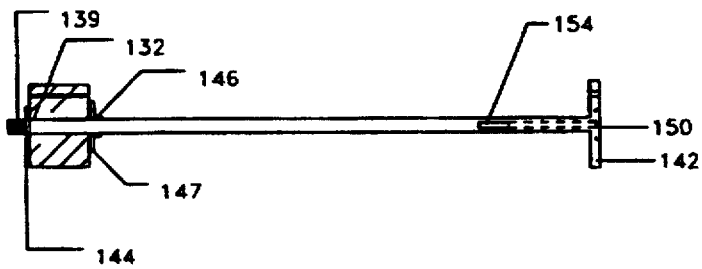
FIG. 16A is a cross sectional view of a plunger assembly in accordance with another embodiment of the present invention.
Figure 16B:
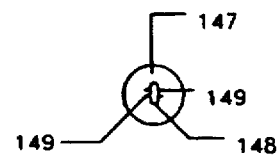
FIG. 16B is an end view of the plunger of FIG. 16A.

Another embodiment of the plunger assembly 130 is shown in FIGS. 16A and 16B. The tip 138 of actuator 134 includes an enlarged flange 144 which engages the front of plunger head 132 to prevent the actuator from being pulled from the plunger when retracted prior to use. The actuator tip 138 is provided with a threaded plug 139 to prevent inadvertent removal of the plug from the outlet during handling of the syringe. The threaded plug 139 may be used with the chamber 10 shown in FIG. 14, with the threaded plug being force fit into the outlet 118. The plug 139 may also be used with a chamber (not shown) having a threaded outlet. Depending upon the material employed and the height of the threads, the plug may be pushed into the outlet with the threads slipping into interengagement or the plug may be twisted into the threaded outlet. The plug 139 may be removed from the outlet by forcefully retracting the actuator 134 or by twisting the actuator to unscrew the plug from the outlet for sealing the outlet to the chamber. The actuator 134 further includes oppositely disposed beads 146 which project from the elongate body 136 of the actuator. The actuator body 136 and beads 146 are movable through the resilient plunger 132 as the actuator is retracted from the chamber of the syringe.

The actuator 134 engages a backplate 147 of plunger 132 to drive the plunger through the plunger and expel liquid from the syringe. The backplate 147 may be a separate component or, if desired, may be provided by the cap 124 shown in FIG. 14. The backplate 147 is formed with an elongated opening 148 which is shaped to permit passage of the actuator body 136 and beads 146 when the beads are substantially aligned with the longitudinal axis of the opening 148. Once the beads have been pulled through the opening 148, the actuator 132 is rotated about 90° to position the beads 146 between a pair of spaced ridges 149. The beads 146 engage the backplate 147, allowing the actuator to drive the plunger 132 through the chamber when the actuator is moved in a forward direction. While the ridges 149 prevent inadvertent rotation of the actuator 134 during use of the syringe, it is to be understood that the configuration of the backplate 147 may be subject to considerable variation.

With the plunger assembly 130 of the present invention, the actuator 134 is initially movable relative to the plunger head, allowing the actuator to seal the outlet of the filled chamber, simplifying the structure of the syringe, and allowing the actuator to be substantially positioned within the chamber to reduce the overall size of the syringe. After the actuator is retracted from the chamber, the actuator engages the plunger head for driving the plunger through the chamber. While the figures illustrate two embodiments of a plunger assembly 130, it is to be understood that the actual configuration of the assembly and the engagement means used to secure the plunger to the actuator are subject to considerable variation within the scope of this invention.

The chamber, as supplied to the consumer, is filled with an injection fluid. Preferably, the prefilled chamber 10 contains a measured amount of fluid for a single injection. Supplying the fluid in pre-measured quantities offers several advantages including improving the efficiency of the injection process, minimizing the risk of injecting an improper amount of fluid, and reducing waste of the injection fluid. However, if desired the syringe may contain more than one application of the injection fluid.

The syringe 6 preferably includes means for filling the chamber 10 with fluid prior to shipment. In the embodiment shown in FIGS. 14–21, actuator 134 is formed with a conduit 150 having an outer opening 152 (FIG. 15B) formed in the push plate 142 and an inner opening 154 formed in the elongate body 136 of the actuator. The inner opening 154 is located so that when the actuator is fully inserted into the chamber 10 as shown in FIG. 14, the inner opening 154 is spaced inwardly of the plunger 132. A hollow tube (not shown) is preferably inserted through bore 156 defined by holes formed in the push plate 142, the cap 124 and the plunger head 132 to permit air to escape from the chamber during filling. Plunger 132 is preferably formed of a material which seals the opening in the plunger when the tube is withdrawn. The chamber 10 may be filled with fluid by injecting the fluid through the conduit 150. After the chamber has been filled, the opening 152 is sealed by a plug, membrane of other suitable means.

Other means may be used to fill the chamber with fluid. The side wall of the chamber may be formed with a port for filling the chamber. The port may be sealed by a plug, membrane or other sealing member after the chamber 10 had been filled with the injection fluid. The conduit 110 may also be used to fill the chamber with fluid by positioning the actuator 134 with the shaped end 138 spaced from the opening 118. Once the chamber is filled, the actuator is fully inserted into the chamber to bring the shaped end 138 into sealing engagement with the conduit 110.

Figure 25:
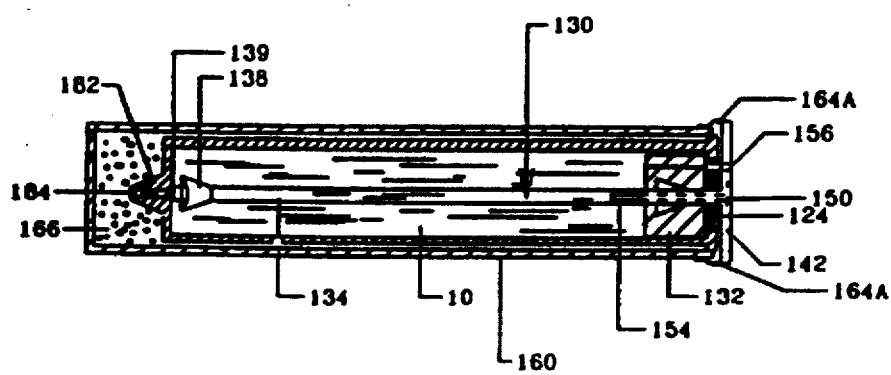
FIG. 25 is a cross-sectional view of a syringe assembly in accordance with another embodiment of the invention, shown packaged for shipment and storage.

As is shown particularly in FIG. 14, the syringe 6 may be enclosed within an outer package 160 sealed to the exterior flange 162 of chamber 10 and an outer cap 164. Package 160 and cap 164 provide a sterile environment protecting syringe 6 from the risk of contamination. The construction of the sterile packaging is subject to considerable modification within the scope of the present invention. For example, the outer cap 164 may be eliminated. FIG. 25 shows an embodiment in which a seal membrane 164A which extends between the package 160 and the push plate 142 to seal the outer package 160 to the chamber 10 and the push plate 142. In the embodiment shown in FIG. 25, the push plate 142 preferably has a diameter equal to or larger than the diameter of the chamber 10. In other modifications of the invention, the push plate 142 may fit within the outer package 160.

When the actuator 134 is retracted, removing the plug 139 of the shaped tip from the opening 118, a small amount of air will be pulled through the conduit and into the chamber 10. This air may be easily expelled from the chamber by pointing the needle 30 in an upward direction and depressing the plunger assembly 130 until liquid flows through the needle as is known in the art. In some applications, it may be desirable to isolate the injection fluid within the chamber from contaminants which may be carried by the air. As is shown particularly in FIG. 14, the space between the syringe 6 and the outer package 160 may be filled with a quantity of a sterile, inert gas generally indicated at 166., After the outer cap 164 is removed but before the seal between the outer package 160 and the flange 162 is broken, the actuator 134 is moved to the fully retracted position drawing some of the sterile air into the chamber as is shown in FIGS. 18 and 19. Once the actuator 134 is fully retracted, the outer package 160 may be removed and the sterile gas expelled from the chamber 10.

Figure 22:
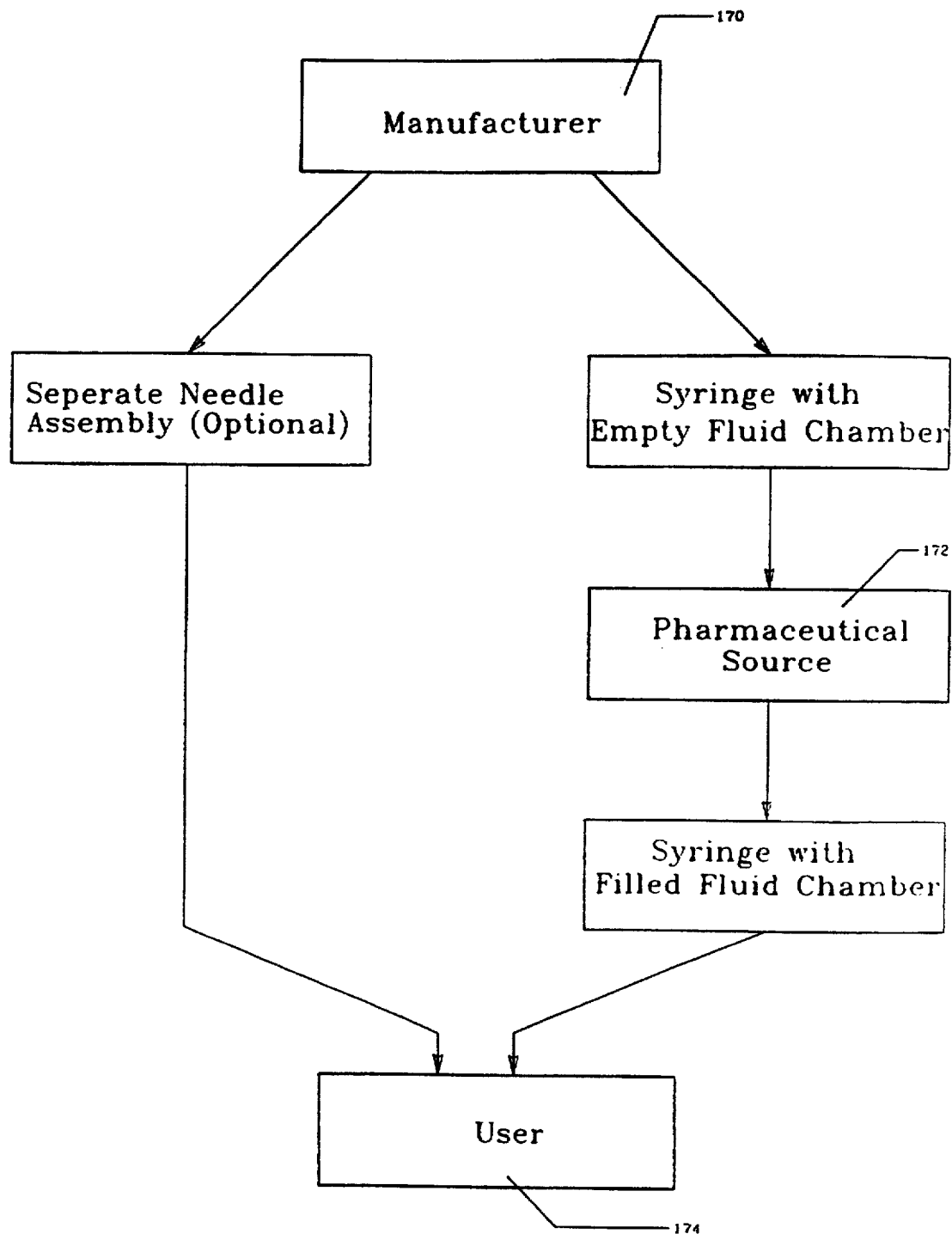
FIG. 22 is a schematic view illustrating the method of supplying a prefilled syringe in accordance with this invention.

FIG. 22 schematically illustrates the method of supplying a prefilled syringe in accordance with this invention. The syringe 6 manufactured by a manufacturer 170 and shipped to a pharmaceutical source 172 where the chamber 10 is filled with injection fluid. The chamber may be filled using a conduit 150 formed in the actuator 134, a port formed through the wall of the chamber, the conduit 110 in the front end of the chamber 10, or other suitable means. After filling, a sterile plug, membrane or other sealing member may be applied to seal the openings to the chamber 10. If the conduit 150 is employed to fill the chamber 10, the outer package 160 may be sealed to the chamber and filled with sterile gas by the manufacturer 170. With the other filling methods, sterile outer packaging may be applied at the pharmaceutical source 172 after the chamber has been filled. The pharmaceutical source 172 may also apply the outer cap 164 or seal membrane 164A to the syringe 6.

The filled syringe 6 is shipped, directly or indirectly, from the pharmaceutical source 172 to the user 174 which may be a hospital, urgent care center, doctor's office, ambulance, patient, or the like. The user pulls the actuator 134 into engagement with the plunger head 132, removes the sterile packaging, moves the needle assembly 8 into the ready position and expels any air from the chamber. The syringe 6 is now prepared for the injection.

In the embodiment shown in FIGS. 14-21, the sheath 22 is detachable from the chamber 10. The chamber 10 and sheath 22 may be supplied to the pharmaceutical source 172 in a single package with the needle assembly 8 coupled to the chamber. The two components may be supplied separately to the source 172. Alternatively, as is indicated in FIG. 22, the manufacturer 170 may supply the needle assembly 8 directly to the user 174 and the empty chamber 10 to the pharmaceutical source 172, with the user snapping the needle source onto the chamber prior to the injection. As is discussed above, if desired the protective sheath may ago be an integral part of the chamber 10 as is shown for example in FIGS. 1-6.

Figure 20:
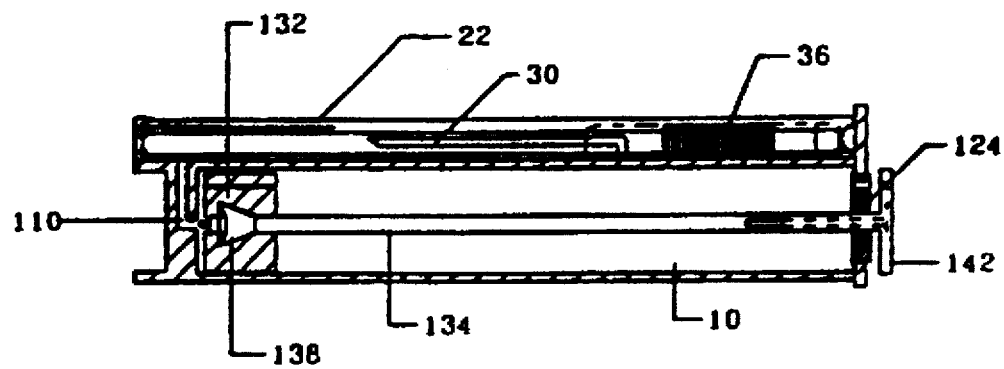
FIG. 20 is a cross-sectional view of the syringe assembly of FIG. 14, shown following an injection with the needle assembly retracted into the protective sheath.
Figure 21:
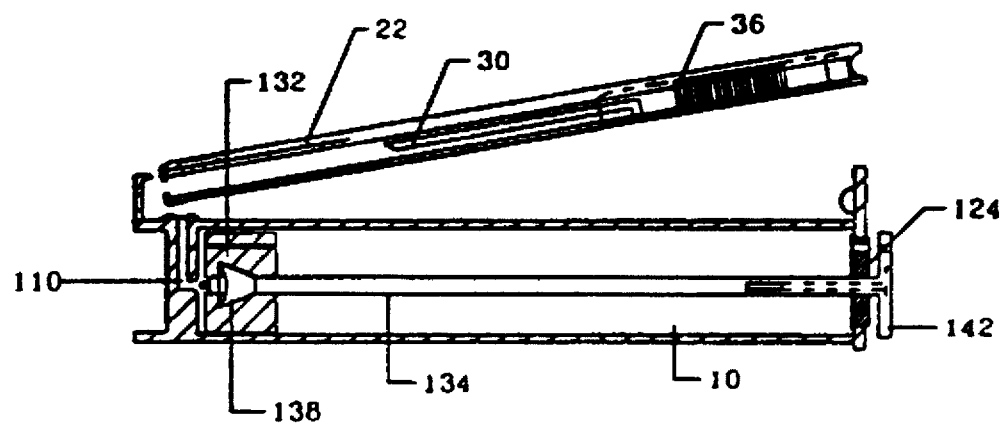
FIG. 21 is a cross-sectional view of the syringe assembly of FIG. 14, shown with the needle assembly detached from the chamber disengaged for disposal.

After the injection, the user 174 retracts the needle 30 into the protective sheath 30 by moving the needle carriage 36 to the disposal position shown in FIGS. 20 and 21. With the syringe 6 of the embodiment shown in FIGS. 14-21, the protective sheath 22 may be removed from the chamber 10 as is shown in FIG. 21 and disposed in the garbage bin designated for sharp objects and the chamber 10 disposed separately. However, it is to be understood that the syringe 6 may be disposed as a single unit if desired.

Utilizing the plunger assembly 130 with the protection system of the previously described embodiments is of particular advantage in that it substantially eliminates the risk of accidental contact with a used needle. Moreover, the needle assembly 8 of this invention may be used to provide syringe 6 with a compact package. The needle 30 may also be efficiently and rapidly deployed with needle assembly 8. However, it is to be understood that plunger assembly 130 of this invention may be advantageously used with other types of needle assemblies.

Figure 23:
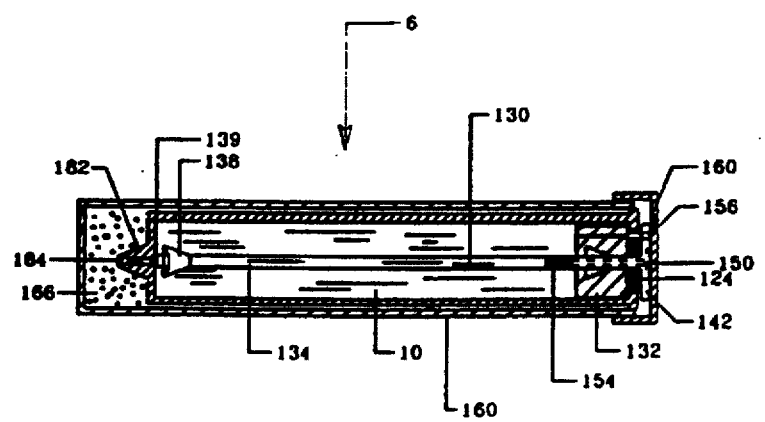
FIG. 23 is a cross-sectional view of a syringe assembly in accordance with another embodiment of the invention, shown packaged for shipment and storage.
Figure 24:
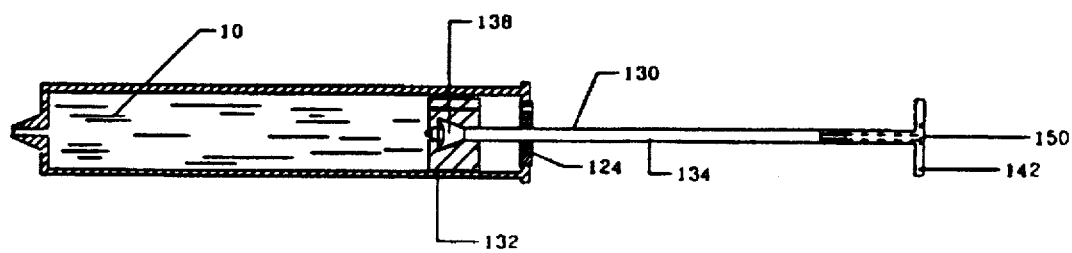
FIG. 24 is a cross-sectional view of the syringe assembly of FIG. 23, shown with the plunger assembly prepared for an injection.

FIGS. 23 and 24 show another embodiment of a syringe 6 in accordance with this invention. The syringe 6 includes a chamber 10 which may be used with the plunger assembly 130 described in relation to FIGS. 14-21. A conical tip 182 provided on the front wall of the chamber 10 is formed with a bore 184 for dispensing fluid from the chamber 10. A needle assembly (not shown) is secured to the conical tip 182 by friction or by a lure locking mechanism as is known in the art. The bore 184 in the chamber is initially sealed by the shaped tip, 138 of the actuator 134. The seal is broken by retracting the actuator from the &amber. The actuator 134 is retracted until the shaped tip 138 is pulled into engagement with the plunger head 132. Thereafter, the plunger assembly 130 may be used to dispense fluid from the chamber as is described in relation to FIGS. 14-21. If desired, the syringe 6 may include outer package 160 sealed to the chamber 10, an outer cap 164, seal membrane 164A or the like, and a sterile gas 166 filling the space between the outer package and the chamber.

While the present invention has been described with reference to a few specific embodiments, the description is illustrative of the invention and is not to be construed as limiting the invention. Various modifications may occur to those skilled in the art without departing from the true spirit and scope of the invention as defined by the appended claims.

What is claimed is:

1. An injection device for use with a needle assembly comprising:

a syringe body having a fluid chamber formed therein for retaining an injection fluid, said syringe body having an outlet for dispensing fluid from said fluid chamber, and a plunger assembly including a plunger slidably disposed in said fluid chamber for creating positive pressures to cause ejection of a fluid from said fluid chamber and an actuator, said actuator being movable relative to said plunger between a first position, with at least a portion of said actuator positioned in said fluid chamber between said outlet and said plunger, and a second position, with said actuator positioned to engage said plunger and drive said plunger through said fluid chamber to create said positive pressures.

2. The injection device of claim 1 in which said actuator includes sealing means for sealing said outlet of said fluid chamber.

3. The injection device of claim 2 in which said sealing means includes a plug shaped to sealingly engage said outlet.

4. The injection device of claim 1 in which said one of said plunger and said actuator includes at least one projection and the other of said plunger and said actuator includes a socket shaped to receive said projection when said actuator is moved to said second position.

5. The injection device of claim 4 in which said projection and said socket are cooperatively shaped to substantially resist removal of said projection from said socket.

6. The injection device of claim 5 in which said projection has a maximum outer diameter and said socket has a minimum inner diameter less than said maximum outer diameter of said socket to prevent removal of said projection from said socket.

7. The injection device of claim 4 in which said actuator includes said projection and said plunger is formed with said socket.

8. The injection device of claim 1, and further comprising an injection fluid retained in said fluid chamber, said actuator extending through said injection fluid when said actuator is in said first position.

9. The injection device of claim 1, and further comprising an outer package assembly substantially enclosing said syringe body.

10. The injection device of claim 9 in which said outer package assembly is sealed to said syringe body, and further comprising a sterile gaseous substance between said syringe body and said outer package assembly.

11. The injection device of claim 1, and further comprising a needle assembly coupled to said syringe body.

12. An injection device for use with a needle assembly comprising:

a syringe body having a fluid chamber formed therein for retaining an injection fluid, said syringe body having an outlet for dispensing fluid from said fluid chamber, and a plunger assembly including a plunger slidably disposed in said fluid chamber for creating positive pressures to cause ejection of a fluid from said fluid chamber and an actuator releasably coupled to said plunger for movement of said actuator between a first position with said actuator released for movement of said actuator through said fluid chamber relative to said plunger and a second position with said actuator in cooperative engagement with said plunger for driving said plunger to create said positive pressures, said actuator including sealing means for sealing said outlet of said fluid chamber, said sealing means being movable away from said outlet for breaking said seal upon retraction of said actuator from said fluid chamber.

13. An injection device for use with a needle assembly comprising:

a syringe body having a fluid chamber formed therein for retaining an injection fluid, said syringe body having an outlet for dispensing fluid from said fluid chamber and a plunger assembly including a plunger slidably disposed in said fluid chamber for creating positive pressures to cause ejection of a fluid from said fluid chamber and an actuator releasably coupled to said plunger for movement of said actuator between a first position with said actuator released for movement of said actuator through said fluid chamber relative to said plunger and a second position with said actuator in cooperative engagement with said plunger for driving said plunger to create said positive pressures, and supply means for filling said fluid chamber with said injection fluid.

14. The injection device of claim 13 in which said supply means includes a conduit formed in said actuator, said conduit providing a passageway between the exterior of said fluid chamber to the interior of said fluid chamber between said outlet and said plunger.

15. The injection device of claim 13 in which said supply means includes a gas release passageway extending between the exterior of said fluid chamber and said fluid chamber between said outlet and said plunger for the release of gas from the interior of said fluid chamber when said fluid is injected into said fluid chamber.

16. An injection device for use with a needle assembly comprising:

a syringe body having a fluid chamber formed therein for retaining an injection fluid, said syringe body having an outlet for dispensing fluid from said fluid chamber, and a plunger assembly including a plunger slidably disposed in said fluid chamber for creating positive pressures to cause ejection of a fluid from said fluid chamber and an actuator releasably coupled to said plunger for movement Of said actuator between a first position with said actuator released for movement Of said actuator through said fluid chamber relative to said plunger and a second position with said actuator in cooperative engagement with said plunger for driving said plunger to create said positive pressures, and further comprising a needle assembly coupled to said syringe body, said needle assembly including a protective sheath mountable to said syringe body and a needle carriage slidably positioned within said sheath, said needle carriage being movable between a forward position with said needle projecting from said front end of said sheath and a retracted position with said needle positioned inside of said sheath.

17. The injection device of claim 16 in which said syringe body has a first longitudinal axis and said sheath has a second longitudinal axis spaced from said first longitudinal axis.

* * * * *